Figure 1:
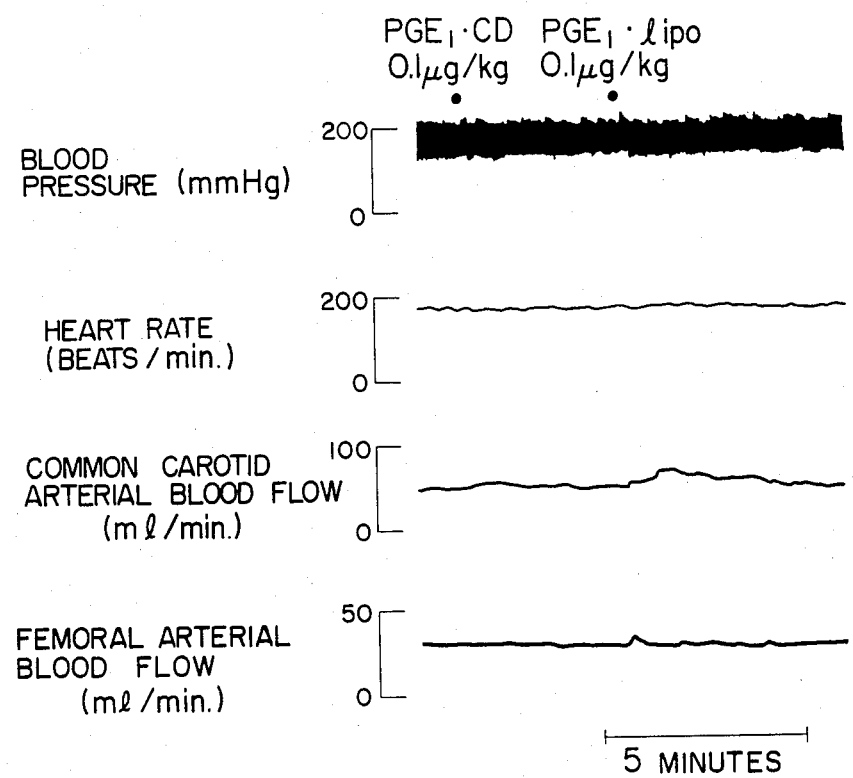

United States Patent [19]

Mizushima et al.

[11] Patent Number: 4,493,847
[45] Date of Patent: Jan. 15, 1985

[54] FAT EMULSION CONTAINING PROSTAGLANDIN $E_1$ AND METHOD FOR PRODUCTION THEREOF

[75] Inventors: Yutaka Mizushima, Tokyo; Hironaka Aihara, Kitamoto; Susumu Otomo, Konosu; Kazumasa Yokoyama, Toyonaka; Hiroyuki Okamoto, Akashi; Tadakazu Suyama, Kyoto, all of Japan

[73] Assignees: Taisho Pharmaceutical Co., Ltd., Tokyo; The Green Cross Corporation, Osaka, both of Japan

[21] Appl. No.: 503,599

[22] Filed: Jun. 13, 1983

[30] Foreign Application Priority Data

Jun. 18, 1982 [JP] Japan ................................. 57-104814

[51] Int. Cl.$^3$ ............................................. A61K 31/19
[52] U.S. Cl. ................................... 424/317; 424/305; 424/365
[58] Field of Search ................................. 424/305, 317

[56] References Cited

U.S. PATENT DOCUMENTS

| | | | |
|---|---|---|---|
| 4,016,290 | 4/1977 | Rahman | 424/199 |
| 4,302,459 | 11/1981 | Steck et al. | 424/199 |
| 4,311,712 | 1/1982 | Evans et al. | 424/199 |

OTHER PUBLICATIONS

Borovan–Chem. Abst.–vol. 95 (1981), p. 91,291w.
Boroyan et al.–Chem. Abst., vol 93 (1980), p. 1136f.

*Primary Examiner*—Sam Rosen
*Attorney, Agent, or Firm*—Cushman, Darby and Cushman

[57] ABSTRACT

A fat emulsion for injection containing prostaglandin $E_1$ which has a vasodilative action as well as a hypotensive action and a method for the production of such an emulsion. The present emulsion is effective in treating chronic arteriostenosis diseases.

13 Claims, 3 Drawing Figures

FAT EMULSION CONTAINING PROSTAGLANDIN E₁ AND METHOD FOR PRODUCTION THEREOF

This invention relates to a fat emulsion containing prostaglandin $E_1$ and a method for the preparation thereof. More particularly, it relates to a fat emulsion containing prostaglandin $E_1$ having a vasodilating action as well as a hypotensive action and a method for the preparation thereof.

Chronic arteriostenosis diseases such as Buerger's disease and occlusive arteriosclerosis are caused by the disorder of blood flow in peripheral blood circulation and are difficult to treat.

Among prostaglandins, prostaglandin $E_1$ (hereinafter referred to briefly as $PGE_1$) is known to exhibit a strong vasodilating action in many mammals, but its insufficient chemical stability has hindered $PGE_1$ from clinical application to the above diseases. When an α-cyclodextrin clathrate compound of $PGE_1$ (hereinafter referred to briefly as $PGE_1 \cdot CD$) which was prepared to improve the stability of $PGE_1$, was employed in the treatment for chronic arteriostenosis diseases, the improvement or cure of frigidity of the affected paw, resting pain, or ulcer was observed in patients whose diseases are not controllable by thoracico-spinal sympathectomy, continuous intra-arterial infusion of a vasodilator or low-molecular dextran, anticoagulation therapy, locally intra-arterial infusion of a steroid, or hyperpressure oxygen therapy. $PGE_1$, however, has a disadvantage of being inactivated by 15-hydroxydehydrogenase existing in lung, kidney and liver. A considerable part of $PGE_1$ is inactivated particularly upon passing through the lung. For this reason, $PGE_1 \cdot CD$ is also unsuitable for intravenous administration. It is, therefore, administered only by the continuous intra-arterial infusion. In the intra-arterial infusion, the arterial incision is necessary to insert a catheter into the artery perfusing through the affected region. Moreover, owing to the acceleration of vascular permeability and proinflammatory action inherent in $PGE_1$, there are sometimes manifested in the administered region such side effects as swelling, dull pain, redness, and fever. As a consequence, the patient is obliged to endure double pain.

As a result of extensive studies to overcome the above difficulties of prior art, the present inventors accomplished the present invention which is predicated upon the discovery that a preparation made by the inclusion of $PGE_1$·in a fat emulsion for intravenous injection (hereinafter such a preparation is referred to as $PGE_1$·lipo) is protected from the inactivation in lung and permits of intravenous administration accompanied with reduced manifestation of side effects in the administered region.

An object of this invention is to provide a $PGE_1$ preparation for intravenous administration with reduced manifestation of side effects in the administered region, as well as a method for the preparation thereof.

Other objects and advantages of this invention will become apparent from the following description.

Figure 2:
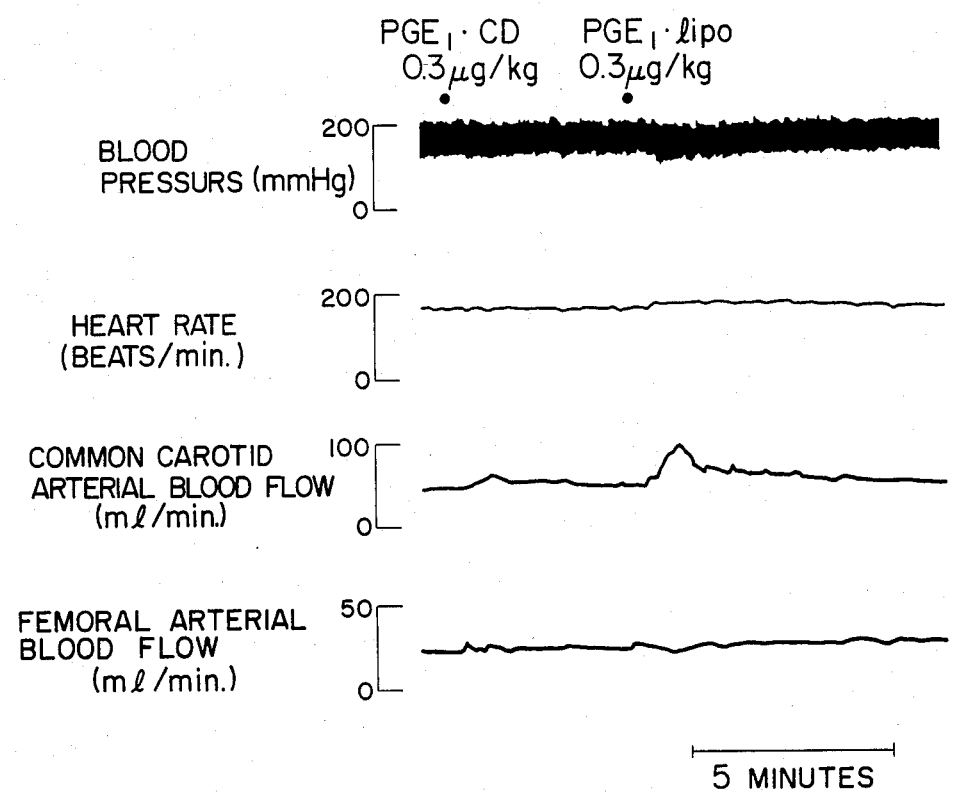
Figure 3:
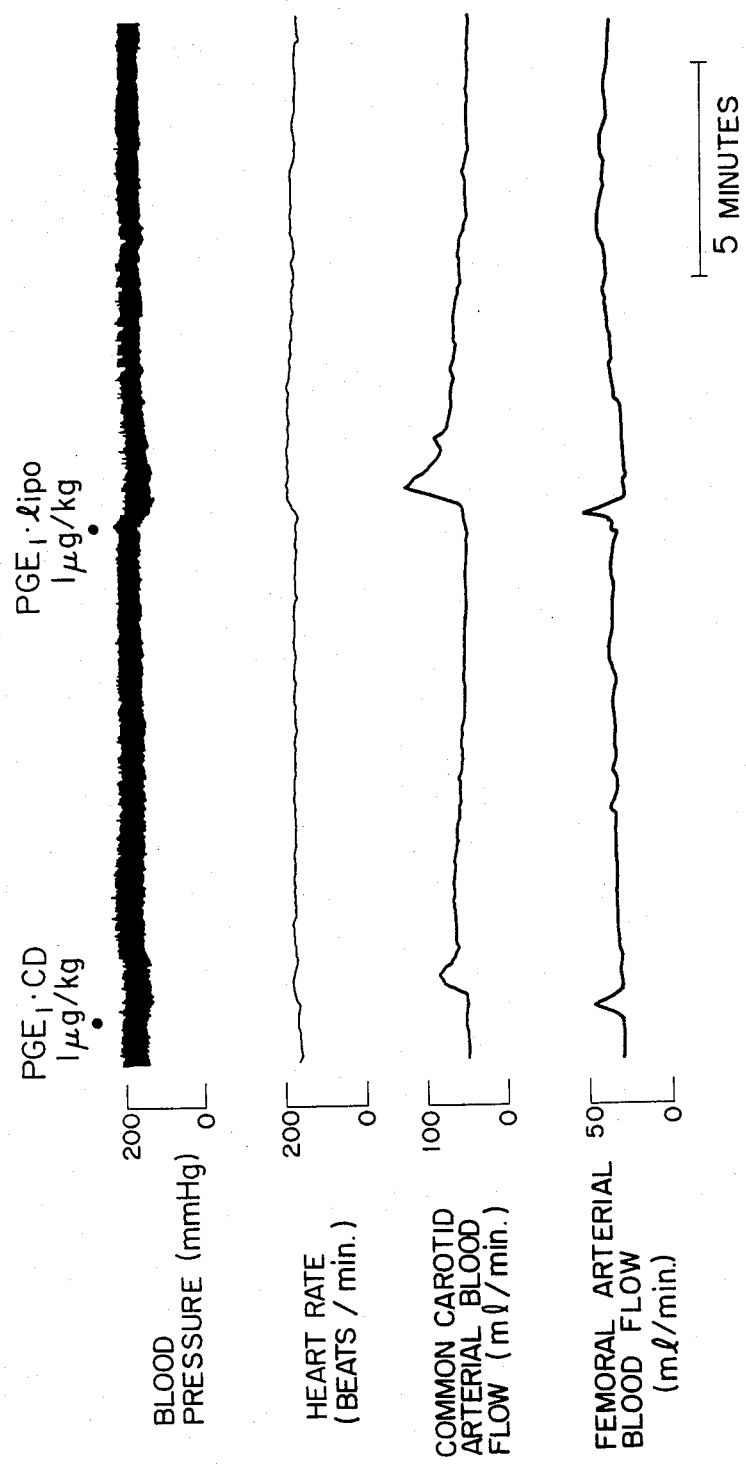

In the accompanying drawings, FIGS. 1 to 3 show the change with time in blood pressure, heart rate, common carotid arterial blood flow, and femoral arterial blood flow, when the present $PGE_1$·lipo or conventional $PGE_1 \cdot CD$ in a dose corresponding to 0.1, 0.3 or 1 μg $PGE_1$/kg is intravenously administered to crossbred male adult mongrel dogs under anesthetia.

According to this invention, there are provided a fat emulsion containing $PGE_1$ and a method for the production thereof.

The fat emulsion, as herein referred to, comprises, as main constitutents, 5–50%(W/V) of soybean oil, 1–50, preferably 5–30, parts by weight of a phospholipid for 100 parts by weight of the soybean oil, and a proper quantity of water. In addition, the fat emulsion may contain, if necessary, emulsifying adjuvant [for example, 0.01–0.3%(W/V) of a fatty acid having 6–22, preferably 12–20, carbon atoms or a physiologically acceptable salt thereof], stabilizers [for example, 0.001–0.5, preferably 0.005–0.1, %(W/V) of a cholesterol or 0.01–5, preferably 0.05–1, %(W/V) of a phosphatidic acid], high-molecular-weight stabilizing adjuvant [for example, 0.1–5, preferably 0.5–1, parts by weight of albumin, dextran, vinyl polymers, nonionic surface active agents, gelatin, or hydroxyethylstarch for 1 part by weight of $PGE_1$], or isotonizing agents (for example, glycerol or glucose in an amount required for the isotonization). The $PGE_1$ content of the present fat emulsion can be suitably varied according to the composition and use of the emulsion, but it should cover the effective amount which is in the range of 100 to 0.2 μg/ml.

The soybean oil for use in the present emulsion is a highly purified soybean oil, preferably that one (purity: 99.9% or above in terms of total glyceride including tri-, di-, and mono-glyceride) obtained by further purifying common refined soybean oil by steam distillation.

The phospholipid, as herein referred to, is a purified phospholipid such as egg yolk phospholipid or soybean phospholipid, which is obtained by the common fractionation technique using an organic solvent. For instance, it is prepared by slowly adding, with stirring, acetone to a crude yolk phospholipid dissolved in a cold n-hexane-acetone mixture, collecting the insolubles by filtration, repeating the procedure of dissolution followed by precipitation, and finally removing the solvent by distillation. The product comprises phosphatidylcholine and phosphatidylethanolamine as major constituents and minor amounts of other phospholipids such as phosphatidylinositol, phosphatidylserine, and sphingomyelin. Various phospholipids can be used each alone or in combinations.

The fatty acids of 6–22 carbon atoms for use as emulsifying adjuvant are those suitable for use in pharmaceuticals. They may be of either straight chain or branched chain. Most preferred are straight chain fatty acids such as stearic, oleic, linolic, palmitic, and myristic acids. The salts should be physiologically acceptable ones such as, for example, salts with alkali metals such as sodium and potassium or with alkaline earth metals such as calcium.

Suitable high-molecular-weight substances for use as stabilizing adjuvant are as follows: The albumin should be of the human origin, in view of the problem of antigenicity. Suitable vinyl polymers include polyvinylpyrrolidone.

Suitable nonionic surface active agents are polyalkylene glycols (for example, polyethylene glycol having an average molecular weight of 1,000–10,000, preferably 4,000–6,000), polyoxyalkylene copolymers (for example, a polyoxyethylene-polyoxypropylene copolymer having an average molecular weight of 1,000–20,000, preferably 6,000–10,000), polyoxyalkylene derivatives of hardened castor oil [for example, hardened castor oil polyoxyethylene-(40), or -(20), or -(100) ether], and polyoxyalkylene derivatives of castor oil [for example, castor oil polyoxyethylene-(20), or -(40), or -(100) ether].

The present fat emulsion is produced, for example, in the following manner: Predetermined amounts of $PGE_1$, phospholipid, and, if necessary, the afore-mentioned additives are mixed with soybean oil and the mixture is heated at 40° to 75° C. to accelerate dissolution, whereby a homogeneous solution is formed. The solution is mixed with a necessary quantity of water and emulsified at 20° to 80° C. by means of a common mixer (e.g. a homomixer) to form a coarse emulsion. A stabilizer and an isotonizing agent may be added at this stage. The coarse emulsion is then subjected to size diminution treatment at 20° to 80° C. by using a homogenizer (e.g. a homogenizer of the high pressure-jet type such as Manton-Gaulin homogenizer or of the ultrasonic type), resulting in a homogenized, finely dispersed fat emulsion containing $PGE_1$. This emulsion, has an excellent storage stability and the average particle size is $1.0\mu$ or below. The homogenization of a coarse emulsion by means of Manton-Gaulin homogenizer is carried out by passing the coarse emulsion 1 to 2 times through the homogenizer under a first-stage pressure of 100–150 $kg/cm^2$ and then 5 to 15 times under a second-stage pressure of 400–700 $kg/cm^2$.

The present fat emulsion is administered through a parenteral route, preferably intravenously. For instance, a dose of 1 to 100 $\mu g$ in terms of $PGE_1$ is administered once a day by the continuous intravenous infusion at a rate of 0.02–0.2 ng/kg body weight per minute. The present emulsion has a powerful action, the vasodilative effect developed on intravenous administration being about 3 times as large as that of $PGE_1 \cdot CD$. If the hypotensive effect is taken as the criterion of varodilation, the latter is 2 to 9 times as large as that caused by $PGE_1 \cdot CD$. The duration of sustained hypotension is 2 to 30 times as long as that in the case of $PGE_1 \cdot CD$. Moreover, the present emulsion exhibits focus selectivity which permits effective treatment of the patient for the disease. Further, the present $PGE_1$ preparation is not inactivated in the lung which is liable to occur with conventional $PGE_1$ preparations such as $PGE_1 \cdot CD$. As a consequence, it has become possible to administrate $PGE_1$ by intravenous injection which was believed to be impossible with conventional $PGE_1$ preparations. The present emulsion exhibits a steady medicinal effect with a small dose. Resulting in reduced side effects. In addition, there is observed none of those swelling, dull pain, redness, and fever which are apt to occur in the region where a conventional $PGE_1$ preparation was introduced.

As described above, the fat emulsion of the present invention having a vasodilative action as well as a hypotensive action is useful as a remedy for chronic arteriostenosis diseases.

The invention is illustrated below in detail with reference to Test Example demonstrating the excellent action of the present fat emulsion, and to Examples of preparative procedures for the present fat emulsion.

TEST EXAMPLE

A group of 4–6 male adult mongrel dogs each weighing about 10 kg was used in each test. The dog was anesthelized with sodium pentobarbital (35 mg/kg, Intravenous injection). Sixty minutes after the anesthesia, the blood pressure (mmHg), heart rate (beats/minute), common carotid arterial blood flow (ml/minute), and femoral arterial blood flow (ml/minute) were measured. After additional 30 minutes, the present fat emulsion ($PGE_1$·lipo) prepared as in Examples described hereinafter or $PGE_1 \cdot CD$ prepared according to the conventional method is administered intravenously or intra-arterially in an amount of 0.1, 0.3 and 1 $\mu g/kg$ to respective dog groups. During sixty minutes, after the administration, each dog was examined for the blood pressure, heart rate, common carotid arterial blood flow and femoral arterial blood flow. In Table 1 is shown the ratio of the effectiveness of $PGE_1$ ·lipo to that of $PGE_1 \cdot CD$ with respect to the degree of decrease in blood pressure and the duration of sustained hypotension in both cases of intravenous administration and intra-arterial administration. The changes with time in blood pressure, heart rate, common carotid arterial blood flow, and femoral arterial blood flow, when $PGE_1$·lipo or $PGE_1 \cdot CD$ was intravenously administered in a dose of 0.1, 0.3 and 1 $\mu g/kg$ in terms of $PGE_1$ were as shown in FIGS. 1, 2 and 3, respectively.

As shown in FIGS. 1, 2 and 3, the vasodilative effect and the hypotensive effect of $PGE_1$·lipo in intravenous administration were about 3 times as large as those of $PGE_1 \cdot CD$; moreover $PGE_1$·lipo was kept from inactivation in the lung to a greater extent than $PGE_1 \cdot CD$. As is apparent from FIGS. 1, 2 and 3, the decrease in blood pressure is linked with the vasodilation and so the hypotensive effect is resulted from the vasodilative effect. By comparison of $PGE_1$·lipo with $PGE_1 \cdot CD$, it is seen from Table 1 that in the intra-arterial administration, both shows nearly the same effect, whereas in the intravenous administration, the hypotensive effect of the former is 2–9 times as large as that of the latter and the duration of sustained hypotensive effect is 2–30 times as long as that of the latter.

TABLE 1

| | | Dose ($\mu g/kg$) | Effectiveness ratio ($PGE_1$·lipo/$PGE_1 \cdot CD$) |
|---|---|---|---|
| Hypotensive effect | Intraveneous | 0.1 | 9.5 ± 5.4 |
| | | 0.3 | 2.7 ± 0.7 |
| | | 1 | 2.3 ± 0.3** |
| | Intra-arterial | 0.1 | 0.7 ± 0.1 |
| | | 0.3 | 0.6 ± 0.2 |
| | | 1 | 1.1 ± 0.3 |
| Duration of sustained hypotensive effect | Intravenous | 0.1 | 31 ± 17 |
| | | 0.3 | 9.2 ± 6.2 |
| | | 1 | 2.1 ± 0.4* |
| | Intra-arterial | 0.1 | 0.9 ± 0.3 |
| | | 0.3 | 1.1 ± 0.4 |
| | | 1 | 1.0 ± 0.1 |

Note:
*$P < 0.05$.
**$P < 0.01$.
These signs show that the numerical values of ratios of $PGE_1$·lipo to $PGE_1 \cdot CD$ with respect to effectiveness and duration of sustained effect are significant at levels of significance of 5% and 1%, respectively.

EXAMPLE 1

To 30 g of purified soybean oil, were added 3.6 g of yolk phospholipid, 900 $\mu g$ of $PGE_1$, 0.15 g of sodium oleate, and 0.15 g of phosphatidic acid. The mixture was heated at 75° C. to form a solution. To the solution, was added 200 ml of distilled water, followed by 7.5 g of glycerol of the official grade (Pharmacopoeia of Japan). The mixture was made up to 300 ml with water for injection at 20°–40° C. and coarsely emulsified in "Homomixer". The coarse emulsion was homogenized by passing 10 times through a Manton-Gaulin-type homogenizer under a first-stage pressure of 120 $kg/cm^2$ and a total pressure of 500 $kg/cm^2$. There was obtained a homogenized, finely dispersed fat emulsion containing PGE$_1$. The emulsion, 0.2-0.4μ in average size of dispersed droplets, contained none of the droplets of 1μ or above in size.

EXAMPLE 2

An emulsion was prepared following the same recipe and the same procedure as in Example 1, except that sodium oleate was not used. There was obtained a homogenized, finely dispersed fat emulsion containing PGE$_1$. The emulsion, 0.2-0.4μ in average size of dispersed droplets, contained none of the droplets of 1μ or above in size.

EXAMPLE 3

Emulsification was performed following the same recipe and the same procedure as in Example 1, except that 0.15 g of cholesterol was used in place of 0.15 g of phosphatidic acid. There was obtained a homogenized, finely dispersed fat emulsion containing PGE$_1$. The emulsion, 0.2-0.4μ in average size of dispersed droplets, contained none of the droplets of 1μ or above in size.

EXAMPLE 4

An emulsion was prepared by using the same recipe and procedure as those in Example 1, except that 90 g of the purified soybean oil was used. There was obtained a homogenized, finely dispersed fat emulsion containing PGE$_1$. The emulsion, 0.2-0.4μ in average size of dispersed droplets, contained none of the droplets of 1μ or above in size.

EXAMPLE 5

An emulsion was prepared by using the same recipe and procedure as those of Example 1, except that 9 mg of PGE$_1$ was used. There was formed a homogenized, finely dispersed emulsion containing PGE$_1$. The emulsion, 0.2-0.4μ in average size of dispersed droplets, contained none of the droplets of 1μ or above in size.

EXAMPLE 6

Emulsification was performed by using the same recipe and procedure as those of Example 1, except that 900 μg of albumin, used as high-molecular-weight substance, was additionally used. There was obtained a homogenized, finely dispersed emulsion containing PGE$_1$. The emulsion, 0.2-0.4μ in average size of dispersed droplets, contained none of the droplets of 1μ or above in size.

What is claimed is:

1. A fat emulsion containing prostaglandin E, which comprises 5-50%(W/V) of soybean oil, an effective amount of prostaglandin E$_1$, 1-50 parts by weight of a phospholipid for 100 parts by weight of the soybean oil, and a proper amount of water.

2. A fat emulsion according to claim 1, which contains as emulsifying adjuvant, 0.01-0.3%(W/V) of a fatty acid having 6-22 carbon atoms or a physiologically acceptable salt thereof.

3. A fat emulsion according to claim 1, which contains as stabilizer, 0.001-0.5%(W/V) of a cholesterol or 0.01-5%(W/V) of a phosphatidic acid.

4. A fat emulsion according to claim 1, which contains as stabilizing adjuvant, 0.1-5 parts by weight of at least one high-molecular-weight substance selected from the group consisting of albumin, dextran, vinyl polymers, nonionic surface active agents, gelatin, and hydroxyethylstarch for 1 part by weight of prostaglandin E$_1$.

5. A fat emulsion according to claim 1, which contains an isotonizing agent.

6. A method for producing a fat emulsion containing prostaglandin E$_1$, which comprises dissolving prostaglandin E$_1$ and a phospholipid in soybean oil, mixing the resulting solution with a proper amount of water to form a coarse emulsion, and homogenizing the coarse emulsion.

7. A method according to claim 6, wherein a fat emulsion comprising an effective amount of prostaglandin E$_1$, 5-50%(W/V) of soybean oil, 1-50 parts by weight of a phospholipid for 100 parts by weight of the soybean oil, and a proper amount of water is produced.

8. A method according to claim 6, wherein the homogenization is performed by passing the coarse emulsion through a high pressure-jet type homogenizer 1-2 times under a first-stage pressure of 100-150 kg/cm$^2$ and then 5-15 times under a second-stage pressure of 400-700 kg/cm$^2$.

9. A method according to claim 6, wherein the dissolution, mixing, and homogenization are carried out at 20°-80° C.

10. A method according to claim 6, wherein 0.01-0.3%(W/V) of a fatty acid having 6-22 carbon atoms or a physiologically acceptable salt thereof is added as emulsifying adjuvant in the dissolution step.

11. A method according to claim 6, wherein 0.001-0.5%(W/V) of a cholesterol or 0.01-5%(W/V) of a phosphatidic acid is added as stabilizer of fat emulsion in the dissolution step.

12. A method according to claim 6, wherein 0.1-5 parts by weight of at least one high-molecular-weight substance selected from the group consisting of albumin, dextran, vinyl polymers, nonionic surface active agents, gelatin, and hydroxyethylstarch for 1 part by weight of the prostaglandin E$_1$ is added in the mixing step.

13. A method according to claim 6, wherein an isotonizing agent is added in the mixing step.

* * * * *